United States Patent
Gontier et al.

(10) Patent No.: US 7,350,331 B1
(45) Date of Patent: Apr. 1, 2008

(54) METHOD FOR PRODUCING METABOLITES FROM PLANTS CULTIVATED IN SOIL-LESS MEDIUM

(75) Inventors: Eric Gontier, Germiny (FR); Alain Clement, Nancy (FR); Frederic Bourgaud, Vandoeuvre les Nancy (FR); Armand Guckert, Villers les Nancy (FR)

(73) Assignees: Institut National Polytechnique de Lorraine (INPL), Vandoevre les Nancy (FR); Institut National de la Recherche Agronomique, Paris Cedex (FR)

( * ) Notice: Subject to any disclaimer, the term of this patent is extended or adjusted under 35 U.S.C. 154(b) by 327 days.

(21) Appl. No.: 10/129,611

(22) PCT Filed: Nov. 7, 2000

(86) PCT No.: PCT/FR00/03095

§ 371 (c)(1),
(2), (4) Date: May 8, 2002

(87) PCT Pub. No.: WO01/33942

PCT Pub. Date: May 17, 2001

(30) Foreign Application Priority Data

Nov. 8, 1999 (FR) .................................. 99 14204

(51) Int. Cl.
*A01G 31/00* (2006.01)

(52) U.S. Cl. .......................................................... 47/59
(58) Field of Classification Search ................. 47/58.1, 47/62, 62 R, 62 N, 58.11, 62 A; 435/289.1, 435/308.1; 210/195.1
See application file for complete search history.

(56) References Cited

U.S. PATENT DOCUMENTS 4,075,785 A * 2/1978 Jones ............................. 47/64

(Continued)

FOREIGN PATENT DOCUMENTS

FR        2758563 A  *  7/1998

(Continued)

OTHER PUBLICATIONS

Liu, D L and J V Lovett. Biologicially Active Secondary Metabolites of barley: I. Developing techniques and assessing allelopathy in barley. Australia Journal: Journal of Chemical Ecology 19(10): pp. 2217-2230 1993.*

(Continued)

*Primary Examiner*—Wendy C Haas
(74) *Attorney, Agent, or Firm*—Young & Thompson

(57) ABSTRACT

A method for producing molecules from plants, characterized in that the plants are cultivated in soil-less conditions and are supplied with a nutrient solution and/or sprayed with a leaching liquid, the solution and/or the liquid being subsequently recovered and treated to extract therefrom certain specific molecules which it contains and which have been released by the roots and/or top growth of the plants.

17 Claims, 3 Drawing Sheets

U.S. PATENT DOCUMENTS

Figure 1:
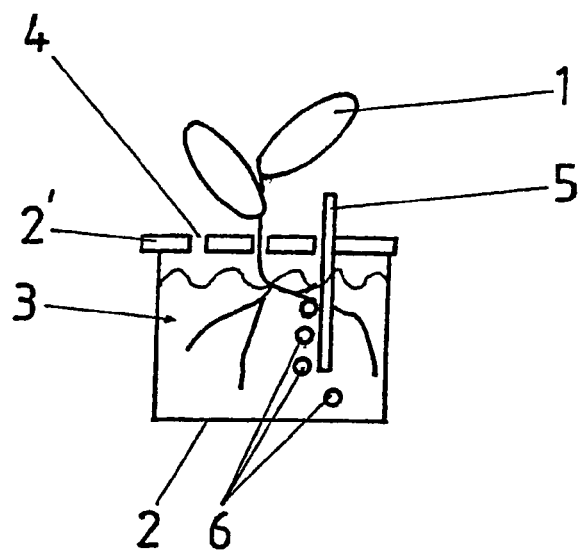

| | | | |
|---|---|---|---|
| 5,010,686 A * | 4/1991 | Rivest | 47/62 C |
| 5,244,794 A | 9/1993 | Prince et al. | |
| 5,279,953 A * | 1/1994 | Stahlhut | 800/294 |
| 5,310,672 A | 5/1994 | Wann et al. | |
| 5,407,816 A * | 4/1995 | Bringi et al. | 435/123 |
| 5,413,928 A * | 5/1995 | Weathers et al. | 435/123 |
| 5,557,884 A * | 9/1996 | Deppe | 47/62 E |
| 5,698,423 A * | 12/1997 | Holowach-Keller et al. | 435/119 |
| 5,908,549 A * | 6/1999 | Wigen | 210/126 |
| 5,992,090 A * | 11/1999 | Stutte et al. | 47/58.1 R |
| 6,021,602 A * | 2/2000 | Orsi | 47/62 A |
| 6,096,307 A * | 8/2000 | Braswell et al. | 424/94.1 |
| 6,324,785 B1 * | 12/2001 | Marrs | 47/58.1 |
| 2002/0132021 A1 * | 9/2002 | Raskin et al. | 424/773 |

FOREIGN PATENT DOCUMENTS

| | | |
|---|---|---|
| GB | 2 009 574 | 6/1979 |
| WO | WO 96/34522 | 11/1996 |

OTHER PUBLICATIONS

Liu, D L and J V Lovett. Biologicially Active Secondary Metabolites of Barley: II. Phytotoxicity of barely allelochemicals. Australia Journal: Journal of Chemical Ecology 19(10) pp. 2231-2244 1993.*

Boitel-Conti M.; Gontier, E.: Laberche J.C.; Ducrocq C.; Sangwan-Norreel B.S. Permeabilization of Datura innoxia hairy roots for release of stored tropane alkaloids. Planta Medica. vol. 61, Issue 3, pp. 287-290 1995.*

Weathers, P.J. and R.W. Zobel. Aeroponics for the culture of organisms, tissues and cells—of plants for secondary metabolite production. Biotechnology Advances. vol. 10 No. 1 pp. 93-115 1992.*

Gontier et al. Hydroponic combined with natural or forced root permeabilization: a promising technique for plant secondary metabolite production. Plant Science vol. 163, Issue 4. pp. 723-732 Oct. 2002.* http://www.sigmaaldrich.com/Area_of_Interest/Life_Science/Plant_Biotechnology/Tissue_Culture_Protocols/Classic_Plant_Media.html.*

Raven et al. Biology of Plants, 5th Ed. Worth Publishers, New York, New York, 1992. p. 472.*

* cited by examiner

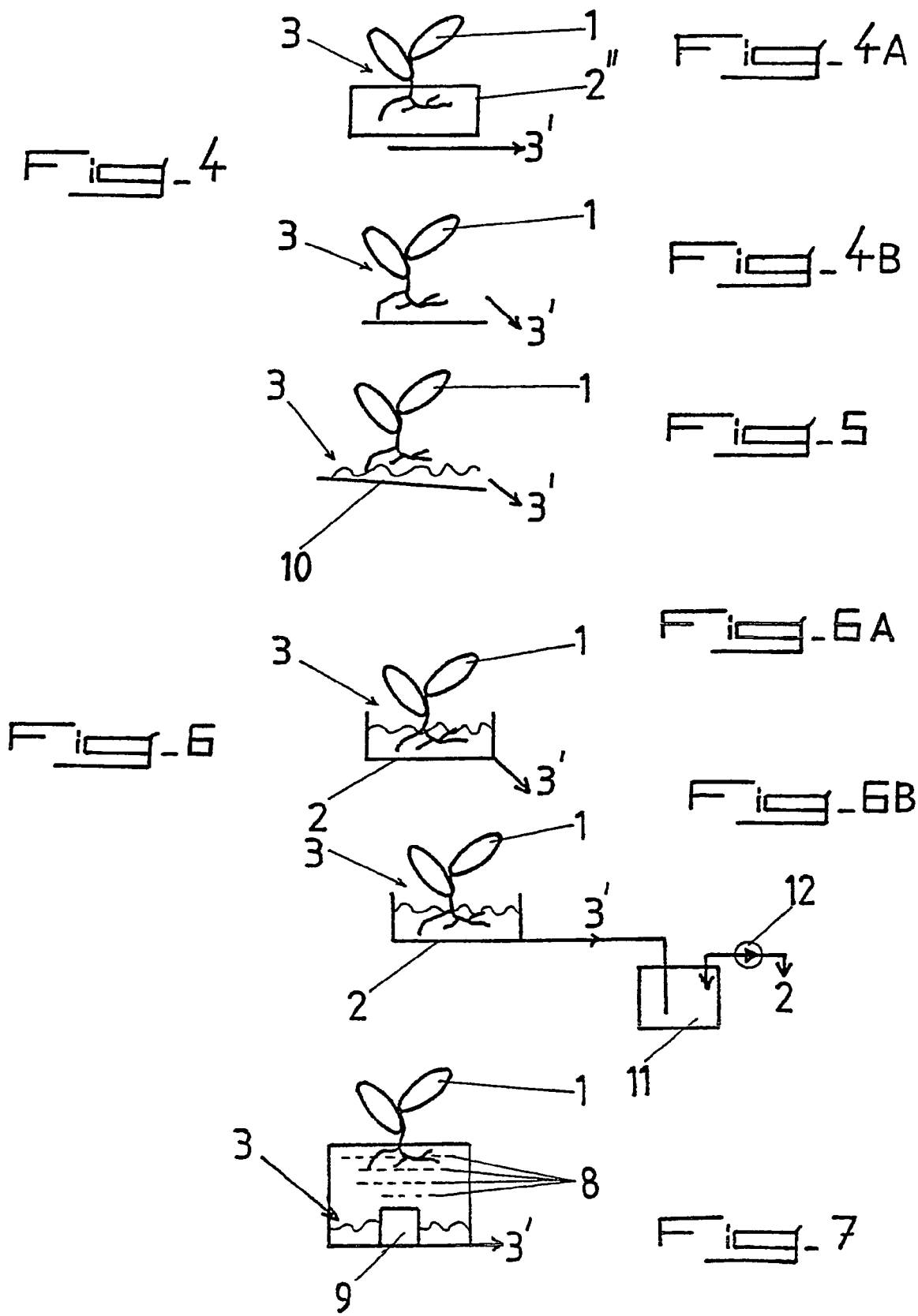

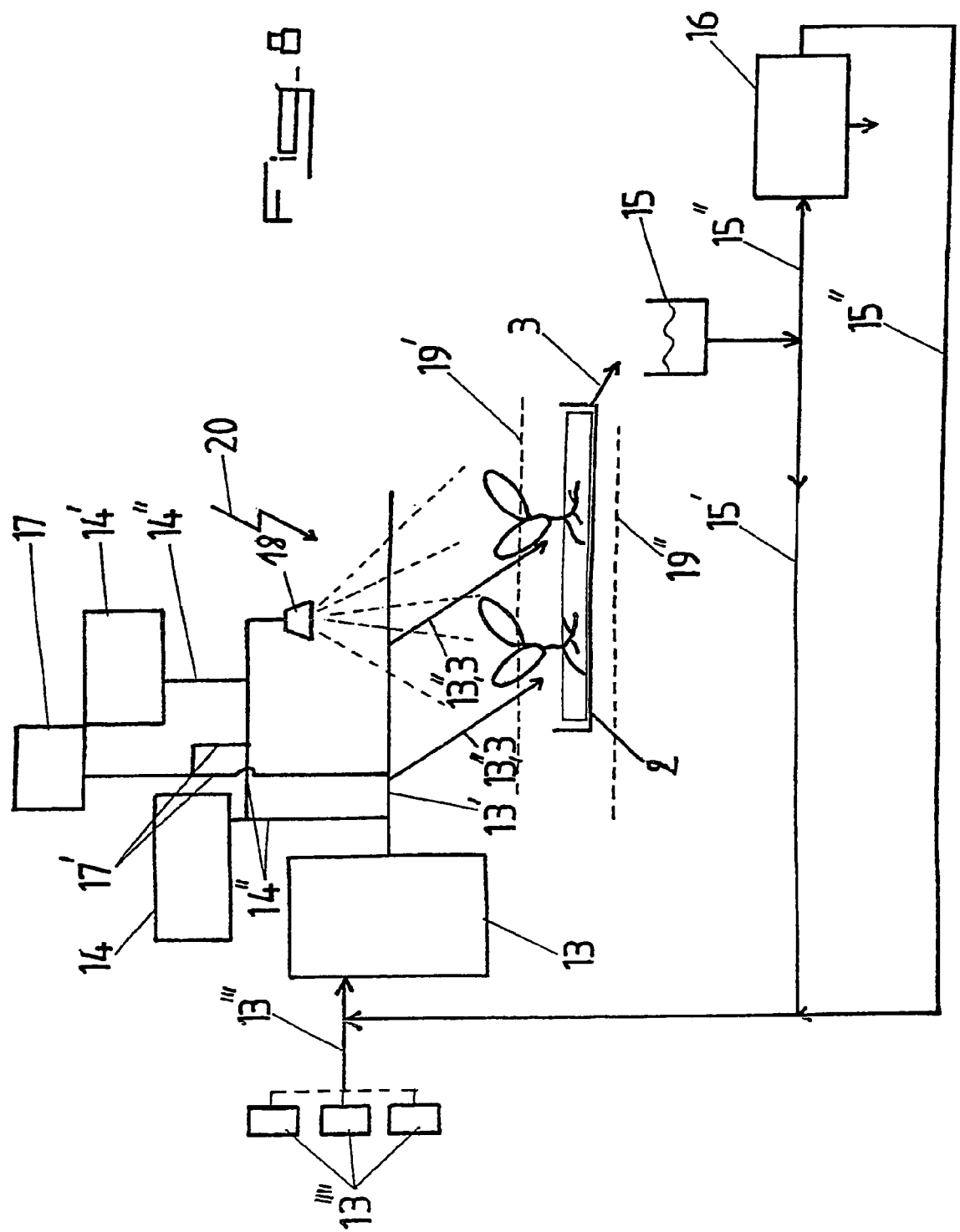

METHOD FOR PRODUCING METABOLITES FROM PLANTS CULTIVATED IN SOIL-LESS MEDIUM

The invention relates to a method of producing metabolites, continuously or semi-continuously, from plants cultivated in a soil-less medium, without losing the viability of said plants, and to an installation for carrying out this method.

Plants produce a large number of the molecules which man uses as drugs, colorants, flavourings, comestible additives or pesticides. These compounds are often typical of a given plant family, genus or species. They are classified as secondary metabolites because they do not always appear to be essential to the survival of the unstressed plant (Bentley 1999, Bourgaud et al 1999, Gontier 1993). Many of these molecules of plant origin serve or have served as a model for chemical synthesis for commercial use. Sometimes, the molecules are complex and extraction from wild plants, plants cultivated in a field or in vitro remain the best sources of supply (Herman 1993).

In particular, cell or tissue culture in bioreactors have been developed for molecules having a high commercial value (price per kilogramme and market volume) (Herman 1993). In this case, the cultures have to be axenic, in other words free from micro-organisms (bacteria and fungi) of which the presence could be harmful to the growth of the plant material and to the production of metabolites thereof. The maintenance of axenic conditions over time is sometimes difficult and leads to significant costs (Gontier 1993). Furthermore, the use of sophisticated systems for in vitro culture (fermenters) adds a cost which is sometimes prohibitory, making the system economically unviable. In vitro biomass production is generally expensive. To make the system cost-efficient, an attempt will be made to produce the maximum of molecules by this biomass without destroying it and while reusing it to the maximum as biocatalyst (Herman 1993).

Production may be stimulated by addition of precursors to the culture medium (Boitel et al 1997), by reversible permeabilisation of the biomass or by physical stress (rise in temperature, change of pH, injury, etc.), chemical stress (addition of $CuSO_4$, $NaCl$, $CaCl_2$, $(NH_4)_2SO_4$ salts or EDTA, DMSO, Tween 20 permeabilising salts, other surfactants or detergents, etc.) or biochemical stress (elicitation, etc.) (Boitel et al 1995-1997, Weather et al 1991, Herman 1993, Mukundan et al 1998).

The object of this manipulation is to force the means of biosynthesis by increasing the overall flow of precursors toward the desired molecule. Numerous publications report extremely positive results obtained by these different means (including Boitel et al 1995-1997, Weather et al 1991, Herman 1993). However, the problem of the axenic nature of the cultures persists.

Other authors describe the use of antifungal and antibiotic cocktails to allow the survival of plant material in the non-axenic state ("plant preservative mixture" commonly called PPM®). In this case, it is difficult to add the microbial inhibitors in such a way that only the bacteria and fungi are affected without an adverse effect on the plant biomass.

In contrast to in vitro culture, the production of molecules from plants which are harvested in the wild or cultivated in fields is an interesting alternative. However, harvesting in the wild can lead to the disappearance of species in the case of over-exploitation (Gontier 1993). It can also give rise to significant variations in the quality and quantity produced. Field cultivation is not always possible owing to a lack of knowledge about the plant or, worse, because it is impossible to obtain a return on investment in the medium term. This is often the case with ligneous plants, for example the yew (Chen and Chen 1997, Ketchum et al 1999), which grows slowly and of which the growth spans decades.

So-called soil-less culture (Morard 1995, Toda et al 1999) in a greenhouse or outside have developed over several years and now allow the highly profitable cultivation of market-gardening or ornamental plants. Progress with these techniques has been dazzling over about fifteen years in terms of devices, nutrient solutions and the control and automation of these systems (Morard 1995). Up until now, the production of secondary metabolites from these cultures, in particular with recovery of naturally or artificially excreted metabolites from the plant roots or even from the top growth has not been attempted or even suggested. In particular, the state of the art does not show or suggest that it is possible a priori to recover such metabolites without them being damaged by the microflora encountered in soil-less culture.

At present, it is not known:

whether plants generally release secondary metabolites from their roots or from their leaves in such a way that this phenomenon may be used for an industrial application;

whether or not it is possible to force natural release of secondary metabolites in cultivated plants, in particular in soil-less culture;

whether a treatment promoting the synthesis and release of said secondary metabolites from plants will affect the survival of said plant in such a way that an industrial application cannot be considered;

whether or not said metabolites are significantly damaged by the microflora capable of developing round plants cultivated in this way.

The object of the present invention is therefore to propose a method of producing molecules from plants which does not necessitate axenic or sterile conditions which allows production of large quantities, is economically viable and does not lead to the, even partial, destruction of the plants in order to extract the desired molecules.

The present invention accordingly relates to a method of producing molecules from plants, characterised in that said plants are cultivated in soil-less conditions and are fed with a nutrient solution and/or are sprayed with a leaching liquid, said solution and/or said liquid then being recovered and treated to extract therefrom certain predetermined molecules that it contains and which have been liberated by the plant roots and/or top growth.

According to a first characteristic of the invention, said method may consist more precisely, of carrying out the following stages:

a) initiation of plant cultivation in soil-less conditions to allow the growth and development of said plants and the obtaining of a sufficiently great biomass to make the method cost effective;

b) recovery of the metabolites liberated by the plant roots or top growth using a liquid which is brought into contact with the roots by percolation or immersion or with the leaves of said plants by spraying;

c) collection of the spent or charged solution in percolated form (in the case of the roots) or leached form (in the case of the leaves) and isolation of the desired molecules contained in this solution by liquid/liquid or liquid/solid extraction, recrystallisation, sublimation or evaporation of the water.

Said method may also comprise an additional stage of forced permeabilisation of the plant roots or top growth with a solution containing, in particular, salts, surfactants, detergents, solvents, elicitors of fungal or bacterial origin, derivatives of jasmonic acid or other products which stimulate the natural defences of plants such that the flows issuing from the roots or the leaves toward the nutrient solution or the leaching liquid are significantly increased without a total loss of viability of said plants so said plants may be reused directly or after a phase of rinsing and return to culture conditions allowing at least the reestablishment of a good physiological state in said plants.

Under these conditions, the method will comprise the following stages a to e:

a) initiation of plant cultivation in soil-less conditions to allow the growth and development of said plants and the obtaining of a sufficiently great biomass to make the method cost effective. The obtaining of this significant biomass, in particular at root level, may be promoted by genetic transformation via *Agrobacterium rhizogenes* (Hooykaas and Schilperoort 1992);

b) permeabilisation of the plant root growth or top growth by chemical treatment (salts, surfactants, detergents, solvents), physical treatment (rise in temperature, etc.) or biochemical treatment (elicitor of fungal or other origin). In the case of chemical or biochemical treatments, this permeabilisation may be carried out using the nutrient solution for the plants or by spraying the top growth;

c) recovery of the metabolites liberated by the plant roots and/or top growth by bringing said plants into contact with a liquid;

d) recovery of the spent nutrient solution or of the charged sprayed liquid (also hereinafter called percolate in the case of permeabilisation via the roots and leachate in the case of permeabilisation via the top growth) and isolation of the desired molecules contained in this solution (percolate or leachate) by evaporation of the water or liquid/liquid extraction (nutrient solution and water-insoluble solvent), liquid/solid extraction (nutrient solution and hydrophilic, hydrophobic, anionic, cationic or other absorbent support having a strong affinity for the desired metabolites) or by recrystallisation;

e) rinsing of the plant root system and/or top growth, then return to growth conditions for just long enough to allow repetition of the treatment.

As a variation of the above-mentioned sequential implementation of the stages of permeabilisation, recovery and resumption which, when looped back over a plurality of repetitive cycles, allows efficient exploitation of said plants, the forced permeabilisation may be carried out continuously by adding a permeabilising solution to the nutrient solution which is delivered continuously or at regular intervals to the plants.

In the latter case, the stages of return to conditions of the plants may be completely eliminated, by using small doses of permeabilising substances and by selecting substances which are not aggressive or stressful for the plants, or at least may be spaced at greater intervals.

After the stage of permeabilisation or an extended phase of permeabilisation, rinsing of the plant root system and/or top growth is carried out, then return to growth conditions for said plants for a time which is just sufficient for carrying out a further forced permeabilisation treatment, followed or accompanied by a stage of recovery of the desired molecules.

It may also be advantageous to increase the biosynthesis capacities of the plant and its potential to release metabolites in the solution by means of a physical treatment selected from the group comprising a rise in temperature, additional or extended irradiation with light, an increase in the $CO_2$ content in the atmosphere in contact with said plant and combinations of a plurality of these physical treatments.

In order to make the method according to the invention even more cost effective, the production and excretion of the metabolites synthesised by the plants may be increased either by neosynthesis of these molecules after the contribution of precursors of these metabolites, these precursors of the means of synthesis of said metabolites being contributed to the plant by the nutrient solution in the region of the roots or by spraying on the top growth in a mixture with surfactants to obtain foliar penetration, or by forcing the photosynthetic activity by means of artificial lighting for a period longer than that to which the plant is accustomed.

According to a first embodiment of the invention, the desired metabolites are liberated by the plants in the region of their roots and are recovered from the spent nutrient solution.

According to a second embodiment of the invention, the desired metabolites are obtained from the top growth of the plants by showering or spraying said plants with a suitable solution or liquid preferably containing surfactants, surface-active agents and/or detergents, the charged showering or spraying solution being recovered separately or in a mixture with the nutrient solution for extraction and purification of the desired molecules.

Preferably, the plants used are selected from the group comprising higher or vascular plants adapted to synthesise economically viable metabolites in a large quantity and in that the desired molecules correspond to secondary metabolites produced naturally by these plants.

The recovered and isolated metabolites are selected from the group comprising tropane and indole type alkaloids, anti-cancer agents, taxanes or taxol derivatives, furocoumarins, terpenes, glycosides, phenyl propanoids, saponines and steroids, and, more generally, non-assimilable or toxic substances in the case of micro-organisms possibly present in the environment of said plants.

According to a further characteristic of the invention, the plants used may be genetically modified to make them produce more metabolites or to modify their morphology by increasing, for example, their root biomass following genetic transformation by *Agrobacterium rhizogenes* or tumefaciens.

The invention will be understood better by means of the following description which relates to preferred embodiments given as non-limiting examples and explained with reference to the accompanying schematic drawings in which 1 to 8 show schematically various ways of carrying out the method according to the invention in conjunction with various material means and devices.

Thus, FIG. 1 shows the system used for example 1 described hereinafter. The plants 1 (Daturas) are cultivated in glass pots 2 filled with nutrient solution 3. The stem of the plants 1 is fixed to the lid 2' of the pots, previously perforated with three holes. One orifice 4 is used for topping up the nutrient solution and the other allows the passage of an air inlet pipe 5 for maintaining good oxygenation of the nutrient solution for the plants by bubbling (bubbles 6).

Figure 2:
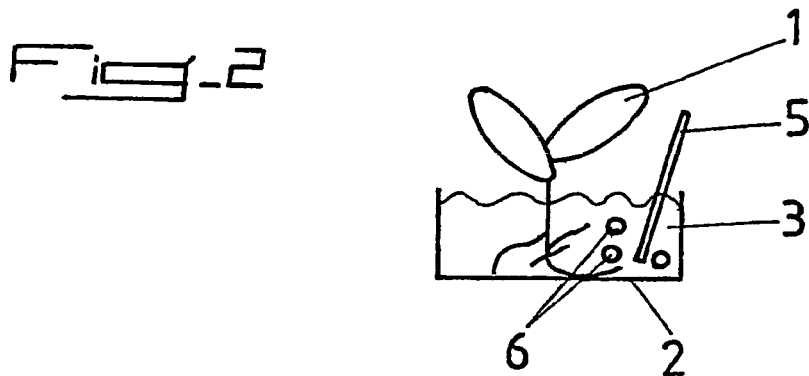

FIG. 2 shows the device used for the cultivation of yews as described hereinafter for example 2. In this case, the plants 1 are placed in the bottom of a PVC (polyvinylchloride) tank 2 filled with nutrient solution 3, and the nutrient solution is oxygenated by the bubbling of air (bubbles 6).

Figure 3:
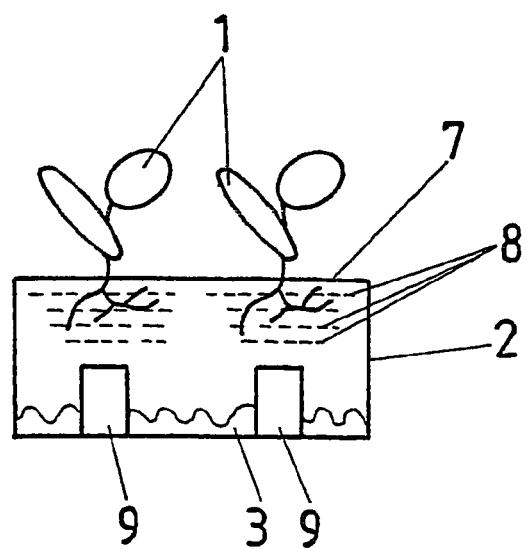

FIG. 3 shows the device used for carrying out the work described in example 4 hereinafter. The plants 1 (Daturas) are placed on perforated plates 7 placed on a PVC culture tank 2. The nutrient solution is sprayed regularly over the roots in the form of a mist 8 by means of programmable atomisers 9.

FIGS. 4 to 7 show various culture devices which may be used for producing metabolites from plants.

More particularly, FIGS. 4A and 4B show culture devices in which the nutrient solution 3 is supplied to the plants 1 by means of capillaries. Once it has come into contact with the roots of said plants, the spent nutrient solution 3', also known as percolate, is drained then recycled. In this case, the plants may be cultivated with or without a substrate 2". This substrate may be of various types such as: rock wool, sand, perlite, vermiculite, reconstituted soil, or of any other type currently used in soil-less culture.

The plants 1 may also be cultivated by the nutrient film technique (NFT). In this case, the nutrient solution 3 is brought to the roots of the plants 1 by trickling (FIG. 5) over a slightly inclined supporting plane 10. The spent nutrient solution 3' is recovered at the end of the trough 10 and this solution may be recycled with or without recovery of the metabolites which it contains.

FIGS. 6A and 6B show soil-less culture systems with immersion of the root systems of the plants 1 in a nutrient solution. The supply of nutrient solution 3 and the drainage of the spent solution 3' may be continuous (continuous system) or discontinuous (discontinuous system). The immersion of the root system may also be continuous (FIG. 6A) with air bubbling in this same nutrient solution or temporary (FIG. 6B). In the second case, drainage may be effected toward a hermetic tank 11 in a low position. This liquid may therefore be transferred by a pump or by a compressor 12 which pushes the solution contained in this hermetic tank 11 toward the culture tank 2, optionally after addition of supplementary substances.

FIG. 7 shows a culture device of the aeroponic type in which the plant roots are regularly sprinkled with the nutrient solution 3 in the form of a mist 8. This mist is obtained using atomisers 9 placed inside the culture tank 2. The spent nutrient solution 3' may be extracted at the bottom.

FIG. 8 is a schematic view of an installation for carrying out, on a large scale and possibly automatically or semi-automatically, the method of producing metabolites according to the invention.

As shown in said FIG. 8, this installation essentially consists on the one hand, of a plurality of containers 2 for the cultivation of plants 1 in soil-less conditions, comprising or not comprising an inert culture support or substrate 2", on the other hand, of a device for the storage and contribution of nutrient solution 3 for the plants 1, comprising a reservoir 13 and a distribution line 13' associated with a network of conduits 13" carrying said solution 3 in a controlled manner to the base of said plants 1, and of a distribution device for permeabilisation solution and/or leaching liquid comprising, in particular, a reservoir for mixing and storage 14 of the permeabilisation solution and/or a reservoir 14' for the leaching liquid, associated with the lines for distribution 14" by spraying and/or injection and, finally, of an assembly of means 15, 15', 15", 16 for recovery, treatment and recycling at least of the spent nutrient solution 3'.

The means for recovery, treatment and recycling advantageously consist of an intermediate storage tank 15 collecting the spent nutrient solution 3' discharged by drainage of the containers 2 for soil-less culture and connected by a direct recycling line 15' and by a second recycling line 15" comprising a unit 16 for separation or extraction of the desired metabolites, in a loop for reinjection into the storage reservoir 13 of nutrient solution 3, this reservoir also being supplied by an injection line 13''' for additional nutrient substances stored in suitable reservoirs 13'''', so as to compensate the quantities of such substances removed by the plants 1'.

To increase the productivity of the installation, it may also comprise a device for distribution of precursor solution of the metabolites to be synthesised by the plants and/or substances stimulating said metabolite synthesis, comprising a storage reservoir 17 and a distribution line 17' connected simultaneously to the distribution line 13' or to the network of conduits 13" delivering the nutrient solution 3 and to means 18 for distribution by spraying of the plants 1 in the region of their top growth similarly to the device 14, 14', 14" for distribution of permeabilisation solution and/or leaching liquid.

According to a further characteristic of the invention, also shown in FIG. 8, the installation may also comprise on the one hand, heating means 19, 19" for the plants 1 and/or their containers 2, for example in the form of networks of parallel spaced conduits traversed by a heat-carrying fluid and extending over and/or under said containers 2 and, on the other hand, means 20 for lighting or artificial insolation of said plants 1.

The mode of operation of the installation shown in FIG. 8 is described in more detail hereinafter.

The nutrient solution 3 is prepared and stored in a first reservoir 13. It is then brought to the base of the plants 1 by a system of increasingly small pipes forming a network of conduits 13". The plants are being cultivated in soil-less conditions, possibly on an inert support 2". The spent nutrient solution 3' flows over a preferably inclined support optionally forming the bottom of the corresponding container 2, this drainage 5 being continuous, cyclical or occasional. This drainage water is recovered in the storage tank 15. It is then recycled directly, or the molecules which it contains are extracted and purified by the unit 16 prior to recycling. A first optional auxiliary reservoir 14 and, if applicable, a second auxiliary reservoir 14' contain(s) permeabilising agents, precursors or other compounds to stimulate the production of metabolites in plants. These products which are possibly mixed with the nutrient solution, are brought into contact with the plants 1 in the region of the roots by percolation (injection into the nutrient solution 3) or in the region of the leaves by spraying. The plants are subjected to natural or artificial lighting 20. The plant top growth and root growth may be heated or cooled by heat-carrying liquids circulating in piping arrangements forming networks 19', 19" or other equivalent means.

In conjunction with the various embodiments of the invention and, in particular, with the embodiment shown in FIG. 8, said method will advantageously consist of three main stages, namely a first stage of culture with the aim of obtaining a large biomass, a second stage promoting the liberation of metabolites by the plants either in the region of their root growth or in the region of their top growth and a third stage aiming to rehabilitate the plants before returning to the aforementioned first or second stage (repetition of cycles).

The present invention accordingly relates to a method and a system for recovering naturally liberated metabolites (permeabilisation not essential) or artificially liberated metabolites (permeabilisation essential) by plants cultivated in soil-less conditions (Morard's definition 1995) with or without unit support (soil-less culture denoting any method of culture apart from culture in solid earth in fields or in the wild). This plant may be cultivated by sprinkling it with a suitable nutrient solution [soil-less culture on a porous support, on a cascade (so-called NFT method according to Morard 1995)], by continuous soaking in the nutrient solution with air bubbling (aquiculture according to Morard 1995) or temporary immersion in said nutrient solution (subirrigation, hydroponics, nutrient film, etc.) or by placing it in contact with said nutrient solution in the form of a mist (aeroponics according to Morard 1995).

If the metabolites are liberated by the plant roots, they will be contained in the nutrient solution (percolate) and therefore recovered by trapping either in a solvent which is immiscible with water or on a support which adsorbs said molecules or else by evaporation or sublimation of the water from the nutrient solution. These various modes of operation may be combined if necessary.

If the metabolites are liberated by the top growth of the plant, with or without permeabilisation, they will be recovered by showering said plants, the showering solution (leachate) being recovered and the metabolites which it contains extracted as mentioned above with respect to the percolate.

In all cases, the water, the spent nutrient solution or the charged leaching liquid may be reused for the cultivation of the plants after topping up the mineral and organic elements required for the growth and secondary metabolism of the plant. If a permeabilising treatment has been carried out, it may be necessary to treat the spent solution (percolate or leachate) correctly before reusing it for a new permeabilising treatment or for reuse as a normal nutrient solution (for plant growth).

When the metabolites have been extracted from the nutrient solution by a solvent which is immiscible with water, the solvent is separated from the aqueous phase and evaporated, and the dry residue is recovered. The metabolites may then be purified and separated from any contaminants. If the metabolites have been trapped on a solid support, this solid support is isolated from the nutrient solution, the metabolites are eluted with an aqueous liquid phase by acting on the ionic force, on the pH or by adding counter-ions or else a water miscible or water-immiscible organic solvent (alcohol, hydrocarbide, organo-chlorinated, nitrile, etc.) is used. In the latter case, the solvents which are most environmentally sound, the least inflammable, the least toxic, the least expensive and the most biodegradable will be preferred. In all cases, all the conventional means of chromatography and of chemistry will be used to purify and concentrate the molecules contained in the eluate.

When the plants have been permeabilised for the time defined as optimal for obtaining the maximum output of metabolites without irreversibly affecting their survival (forced sequential permeabilisation over short periods or gentler permeabilisation over longer periods), the permeabilising treatment is stopped. The plants are returned to normal culture conditions. When they have been treated by a permeabilising solution, a rinsing solution is used to remove this permeabilising agent (surfactant, detergent, salt, acid, base, etc.). This solution temporarily replaces the nutrient solution. Only afterwards are the plants returned to culture under normal conditions. After an adequate period of culture, the plants may be permeabilised again. These cycles may be reiterated until there is a significant reduction in the production, productivity and the health of the plants. In this case, all or some of the culture is replaced by young plants which are subjected to growth with the first permeabilising treatment, preferably until optimum development is obtained.

Continuous permeabilising treatment may be considered in certain cases. In this case, the permeabilising treatment will be sufficiently gentle to allow the output of the metabolites and, in particular, the survival of the plant throughout said permeabilising treatment. When the effectiveness of the treatment begins to drop significantly and causes an economically unacceptable drop in yield, the "old" plants are replaced by younger ones which will be permeabilised immediately or after forcing growth.

Precursors of the desired metabolites may generally be added during permeabilisation of the plants. In this case, these molecules may be biotransformed by the cells of said plant. Precursors should be added moderately so they do not act as a source of carbon for micro-organisms of which the development could compromise the survival of said plants in the long term. These precursors may be added directly into the nutrient solution when the roots are permeabilised. They may be added through the nutrient solution via the roots if the leaves are also permeabilised, but also by foliar means via the plant-showering liquid.

In order further to illustrate the possible practical applications of the method according to the invention, four non-limiting examples thereof will be described hereinafter.

EXAMPLE 1 OF IMPLEMENTATION OF THE METHOD

Production of Tropane Alkaloids from Hydroponically Cultivated *Datura innoxia* Mill The plants used originate from seeds provided by the Institut für Pflanzengenetik und Kultulpflanzenforschung (D-06466 Gatersleben, Corrensstr. 3, Germany). These seeds were scarified in concentrated sulphuric acid for 10 minutes at ambient temperature. After abundant rinsing in running water, they were caused to germinate in pots containing moist soil at a temperature of 25° C.+/−1° C. with a photoperiod of 16 h and hygrometry of 60 to 70%. After two months, when the plants had reached a size of 15 to 20 cm, in other words a stage of 8 to 10 leaves, they were depotted and transferred into glass pots of the type known as "baby food jars" (Sigma-Aldrich Inc., France) of 175 ml. The plants were held by the pot lids, previously perforated with three holes (one for the stem, one for the air bubbling and one for topping up the liquid, see FIG. 1). An MS type nutrient solution diluted four fold (Murashige and Skoog, 1962) was added to the pot. Air could be bubbled into the nutrient solution through silicone tubes in order to maintain good oxygenation of the plant root system and also to avoid the excessive development of populations of micro-organisms. Sixty plants were thus installed. They were cultivated for two weeks under the same conditions of light, temperature and hygrometry as mentioned above.

Increasing doses (0, 1, 2, 3 or 5% V/V—volume by volume) of surfactant (of the type known by the name Tween 20: polyoxyethylenesorbitan monolaurate) were added to the nutrient solution. Permeabilisation using Tween 20 (sold by the company Prolabo) was carried out in the absence of air bubbling (to avoid the formation of foam) for 0, 12, 24 or 48 hours. The nutrient solution of each plant was reharvested, filtered and analysed by gaseous phase chromatography. The average total concentration of hyoscyamine and scopolamine increases gradually with the surfactant concentration. It passes from 7 mg/l without surfactant to 45 mg/l with 5% of Tween 20. The concentration of hyoscyamine and of scopolamine increases with the duration of the treatment.

All the permeabilisation solutions were recovered and the molecules which they contained were taken up in chloroform after addition of ammonia to pH 9. The chloroform was evaporated and the dry residue contained both the two hyoscyamine and scopolamine molecules.

The permeabilised plants were subjected to rinsing of the root system with running water and were returned to hydroponic culture as mentioned above. After three weeks of culture, all the plants had survived. They had continued their growth and some of them which had been permeabilised even experienced greater growth than the control plants.

One month later, the plants which had been permeabilised for the first time were permeabilised a second time under several conditions:

a) 4 control plants (non-permeabilised)

b) 4 plants permeabilised for 24 hours with 3% of a surfactant known by the name of Teepol (registered trade mark—Temana)

c) 4 plants permeabilised for 24 hours with 5% of Tween 20 d) 4 plants permeabilised for 24 hours with 5% of Tween 20 placed under continuous lighting at 27° C.

e) 4 plants permeabilised for 24 hours with 5% of Tween 20 plus 1 g/l of ornithine and 1 g/l of phenylalanine.

The nutrient solutions were removed, filtered and analysed as mentioned hereinbefore.

The concentrations of hyoscyamine and scopolamine were as follows:

a) 1.5 mg/l+/−1
b) 2.4 mg/l+/−11.4
c) 9.1 mg/l+/−4
d) 18.8 mg/l+/−3.7
e) 22.7 mg/l+/−2.4

Conclusion: It is possible to cause Daturas to grow by aquiculture. Daturas spontaneously liberate alkaloids (hyoscyamine and scopolamine) into the nutrient solution. This liberation (also called release hereinafter) may be forced by permeabilising the plants with surfactants. In this case, it is possible to have a permeabilising effect without affecting the survival of said plants by acting on the nature of the surfactant, its concentration and the contact time. Tween 20 is an effective surfactant for this application. In equal doses, Tween 20 is more effective than Teepol. The addition of hyoscyamine and scopolamine precursors is very beneficial in terms of quantity of alkaloids liberated into the nutrient solution. The passage of the plants to continuous lighting for 24 h at a higher temperature gives results close to those obtained with addition of precursors. In this case, it may be felt that optimisation of the system could lead to a further significant increase in the productivity of the method.

The permeabilised plants were rinsed and returned to culture. They all survived and gave rise to subsequent permeabilisation.

It can been seen from the foregoing that plants of the *Datura* type may be cultivated in soil-less conditions so as to produce tropane alkaloids which are recovered in the spent nutrient solution. Production may be increased by carrying out a suitable treatment. This treatment may be carried out using surfactants. The surfactants are not all as effective as each other. The higher the dose of surfactant, the more effective the treatment. The longer the treatment, the more effective it is. A treatment carried out under ideal conditions allows survival of the plant, or even additional development thereof, and it is therefore possible to permeabilise it several times. The effectiveness of the permeabilising treatment may be increased by addition of precursors to the permeabilising solution. This effectiveness may also be increased by forcing photosynthesis by subjecting the plants to continuous lighting, to an increase in the $CO_2$ content and/or by raising the ambient temperature.

EXAMPLE 2 FOR IMPLEMENTATION OF THE METHOD

Production of Taxanes from Yews by Soil-Less Culture

Four yew plants 60 cm in height were purchased commercially, depotted and placed in PVC (polyvinylchloride) pots with a capacity of 6 liters and containing 5 liters of an MS type nutrient solution (Murashige and Skoog, 1962) diluted 12 fold. After 4 days of culture in a greenhouse with air bubbling (0.25 vvm-0.25 volume of gas per volume of medium and per minute) (FIG. 2), the nutrient solution was removed, filtered over 0.45 µm Millex type filters and analysed by high pressure liquid chromatography (HPLC) over a column C18 of 30 cm with a gradient of 0 to 100% of methanol and UV detection at 254 nm. Taxol was not detected in this nutrient solution. The solution was replaced by a fresh solution and 2% of Tween 20 were added to the culture pot of two of the plants. After 24 hours, a concentration of 2.1 mg/l+/−1.04 (that is 5 µg/l/g of fresh substance) was measured in the nutrient solution of the permeabilised plants whereas only 0.2 mg/l+/−0.16 (that is 0.2 µg/l/g of fresh substance) could be measured in the case of non-permeabilised plants. Fairly similar results are obtained with the dosage of baccatine 3 (another secondary metabolite which is of interest in the case of the yew). After rinsing the roots, the plants could be permeabilised again without compromising their viability for at least the three weeks of the experiment. These results therefore show that it is possible to obtain partial liberation of the taxanes (paclitaxel) from yews by soil-less culture (hydroponic culture of the aquiculture type in this case). In our example, neither the nutrient solution nor the permeabilising treatment have been optimised. Even more interesting results can therefore be expected after optimisation of said nutrient solution (see Morard 1995), of the culture conditions (temperature, light, $CO_2$, etc.) and of said permeabilising treatment.

EXAMPLE 3 OF IMPLEMENTATION OF THE METHOD

Production of Furocoumarins from Hydroponically Cultivated Rues (*Ruta graveolens*) (Aquiculture According to Morard 1995)

Eight 10 month old plants cultivated in a pot were cultured in an MS/4 nutrient solution (Murashige and Skoog 1962 solution diluted 4 fold) with air bubbling for two weeks (same device as in FIG. 2). Four of the eight plants were permeabilised for 24 hours with 3% (V/V) of Tween 20. The nutrient solutions were then removed, filtered and analysed by gaseous phase chromatography. The nutrient solution of the permeabilised plants contained on average 8.1+/−4.1 mg/l of furocoumarins (psoralene, 8 methoxypsoralene, 5 methoxypsoralene and 5.8 dimethoxypsoralene) in contrast to 5.2+/−2.8 mg/l in the case of the nutrient solutions of the four control plants. The plant roots were rinsed in water, then the plants were returned to culture for a week. Next, the four plants which had already been permeabilised the first time were permeabilised again in the same way. The results are as follows: 22.5+/−6.1 mg/l in the case of the permeabilised plants versus 19+/−8.5 mg/l in the case of the non-permeabilised plants.

A third permeabilisation was carried out on the same plants and gave similar results with all the plants surviving.

Conclusion: The Rues may be cultivated in soil-less conditions. They naturally release furocoumarins in the nutrient solution but this liberation may be increased by a suitable permeabilising treatment (Tween 20 at 3% in this case). Other types of treatment may be considered in the same way: other surfactants, rise in temperature of the nutrient solution or increase in the salinity of the nutrient solution, addition of umbelliferone or phenylalanine, for example. As in example 2, the culture conditions and the permeabilising treatment may obviously be optimised to give even better yields.

EXAMPLE 4 OF IMPLEMENTATION OF THE METHOD

Aeroponic Culture of *Datura innoxia* and *Datura stramonium*

Seeds of *Datura stramonium* and of *Datura innoxia* were germinated in small cups containing vermiculite sprinkled with nutrient solution. These cups were then transferred into supports composed of perforated (PVC) plates. These plates were placed on a large tank measuring 1.2 m×1 m×1 m, at the bottom of which six atomisers soaked in nutrient solution (FIG. 3). The atomisers went off for 15 minutes every half hour. The entire device was placed in a phytotron under conditions identical to those in example 1. After 1 month of culture, of several tens of grams of fresh substance, the total biomass exceeded a kilogram (stems plus leaves plus roots). HPLC analysis revealed the presence of 8 mg/l of alkaloids in 40 liters of nutrient solution, that is a calculated total of 320 mg of hyoscyamine and scopolamine.

Conclusion: The aeroponic growth of the Daturas is very fast. The plants are healthy and vigorous. Furthermore, they spontaneously release alkaloids into the nutrient solution. This release may be improved by a suitable treatment such as permeabilisation, a change of the nutrient solution with increase in the salt concentration or increase in the incubation temperature of the roots and possibly the addition of precursors of the tropane alkaloids (Gontier 1993).

It follows from the foregoing that Daturas may be cultivated aeroponically and, in this case, the growth of the plant material is very fast. Large quantities of biomass may be obtained in a shorter time than by hydroponics (aquiculture according to Morard 1995). Furthermore, secondary metabolites may be recovered in the spent nutrient solution. The metabolite content of this solution depends on the quantity of biomass and the time for which the nutrient solution is in contact with the root growth of this biomass. An increase in the concentration of metabolites by a suitable treatment (permeabilisation, ionic force, temperature, elicitation) can also be imagined.

Therefore, as it is possible to grow plants over several thousand square meters of greenhouse (in the case of tomatoes and cucumbers) and since it is possible to recycle the spent nutrient solutions (in the case of aquiculture, aeroponics, NFT (nutrient film technique)), the method of the invention can allow cultivation over several thousand square meters of plants which produce secondary metabolites. The metabolites spontaneously released in the spent nutrient solution can be recovered. The liberation of these molecules and the biosynthesis thereof prior to release can also be forced. In the case of plants which produce secondary metabolites which are then "extruded" or "excreted" at the surface of the leaves (Brown and Zobel 1990), these compounds can even be recovered by showering said plants with a suitable solution and recovering the leachates containing the metabolites which are of interest. A device of this type will be used to produce molecules of plant origin, and these molecules can have various applications such as therapeutic, cosmetic, comestible or non-comestible applications. These molecules will preferably have a fairly low molecular weight and need not be completely insoluble in the water which may or may not contain additions of surfactant.

The invention is obviously not limited to the embodiment described and illustrated in the accompanying drawings. Modifications are possible, in particular with regard to the constitution of the various elements or by substitution of technical equivalents, without departing from the scope of protection of the invention.

DETAILED BIBLIOGRAPHY

BENTLEY R., 1999, "Secondary metabolite biosynthesis: the first century", Critical review in Biotechnology, 19, 1, 1-40.

BOITEL-CONTI M., GONTIER E., LABERCHE J. C., DUCROCQ C. and SANGWAN-NORREEL B. S., 1995—"Permeabilization of *Datura innoxia* hairy roots for release of stored tropane alkaloids". Planta Medica, 61, 257-290.

BOITEL-CONTI M., GONTIER E., LABERCHE J. C., DUCROCQ C., SANGWAN-NORREEL B. S., 1996—"Inducer effect of Tween 20 permeabilization treatment used for release of stored tropane alkaloids in *Datura innoxia* Mill hairy root cultures". Plant Cell reports, 16, 241-244.

BOITEL-CONTI M., GONTIER E., ASSAF C., LABERCHE J. C., and SANGWAN B., Cultures de racines in vitro, French patent application 97 00641, 22 Jan. 1997.

BOURGAUD F., BOUQUE V. and GUCKERT A., 1999, "Production of flavonoids by Psoralea hairy root cultures". Plant Cell, Tissue and Organ Culture, 56, 97-104.

BROWN S. A. and ZOBEL A. M., 1990, "Biosynthesis and distribution of coumarins in the plant", Padova, 20-22 Sep. 1990, Italy, Ed: Societa italiana di fitochimica and imprimitur editrice s.n.c., 15-37.

GONTIER E., 1993, "Etude de la production d'alcaloïdes tropaniques chez le *Datura innoxia* Mill. cultivé in vitro: impact physiologique de l'immunobilisation des cellules dans une matrice d'alginate de calcium". Thèse de l'Université de Picardie Jules Verne, pp 200.

HERMAN E. B., 1993, "Recent advances in plant tissue culture II, Secondary metabolite production" 1988-1993, Ed. Herman E. D., Agritech consultants, Inc., Shrub Oak, USA.

HOOYKAAS P. J. J. and SCHILPERORT R. A., 1992, "*Agrobacterium* and plant genetic engineering", Plant Molecular Biology, 19, 15, 15-38.

KETCHUM R. E. B, GIBSON D. M., CROTEAU R. B. and SCHULER M. 1999, "The kinetics of taxoid accumulation in cell suspension cultures of Taxus following elicitation with methyl jasmonate", Biotechnol. and Bioeng, 62, 1, 98-105.

MORARD P., 1995, "Les cultures vĕgĕtales hors sol", publications agricoles Agen, ISBN: 2-9509297-O-2, pp 304.

MUKUNDAN U., BHIDE V., SINGH G. and CURTIS W R, 1998, "pH mediated release of betalains from transformed root cultures of *Beta vulgaris*". Appl. Microbiol. and Biotechnol, 50, 241-245.

MURASHIGE and SCOOG, 1962, "A revised medium for rapid growth and bioassays with tobacco tissue cultures", Physiol. Plant, 15, 473-497.

SHEN Y. C. and CHEN C. Y., 1997, "Taxanes from the roots of Taxus marei". Phytochem., 44, 8, 1527-1533.

TODA T, KOYAMA H. and HARA T., 1999. "A simple hydroponic method for the development of a high viable root system in *Arabidopsis thaliana*.", Biosc. Biotechnol. Biochem. 63, 1, 210-212.

WEATHER P. CHEETHAM R. D. and DILORO A., 1991, "Process for extracting enhanced amounts of plant secondary metabolites with limited loss of plant viability", U.S. Pat. No. 5,413,928.

The invention claimed is:

1. A method of producing molecules from plants with top growth and root growth, comprising the steps of:
    cultivating said plants in soil-less and non-sterile conditions;
    feeding said plants with a nutrient solution and/or spraying said plants with a leaching liquid;
    recovering and treating said solution and/or said liquid to extract therefrom secondary metabolites liberated by roots and/or top growth of said plants, said metabolites being selected from the group consisting of tropane and indole type alkaloids, anti-cancer agents, taxanes or taxol derivatives, furocoumarins, terpenes, glycosides, phenyl propanoids, saponines and steroids;
    recovering said extracted metabolites;
    forcing permeabilization of said roots or top growth with a permeabilizing solution containing salts, surfactants, detergents, solvents, elicitors or fungal or bacterial origin, derivatives of jasmonic acid or other products which stimulate the natural defenses of plants; and
    repeating said steps of forcing permeablization, recovering and treating said solution and/or liquid to extract metabolites, and recovering said extracted metabolites until a desired amount of metabolites have been recovered from said plants, wherein,
    said forcing permeabilization step is carried out continuously by adding said permeabilizing solution to said nutrient solution supplied continuously or at regular intervals to said plants such that flows issuing from said roots and/or top growth, toward and into spent nutrient solution and/or charged leaching liquid contain said metabolites and are significantly increased without loss of viability of said plants,
    said forcing permeabilization step does not lead, even partially, to the destruction of said plants, and
    said plants are genetically modified to produce more metabolites or to increase root biomass following genetic transformation by *Agrobacterium rhizogenes*.

2. The method according to claim 1, further comprising the steps of:
    initiating plant cultivation in soil-less conditions to allow growth and development of said plants;
    recovering said metabolites liberated by said roots or top growth using a liquid which is brought into contact with said roots by percolation or immersion or with leaves of said plants by spraying;
    collecting spent or charged solution in percolated form from said roots or leached form from said leaves;
    isolating desired metabolites contained in said collected solution by liquid/liquid or liquid/solid extraction, recrystallization, sublimation or evaporation of water.

3. The method according to claim 1, further comprising the steps of:
    rinsing of said roots and/or top growth of said plants after forcing permeabilization; and
    returning said rinsed plants to growth conditions for a time which is just sufficient for carrying out a further forced permeabilization treatment, followed or accompanied by a step of recovering said metabolites.

4. The method according to claim 1, further comprising the step of:
    increasing the biosynthesis capacities of said plants and potential to release metabolites in the solution by a physical treatment selected from the group consisting of a rise in temperature, additional or extended irradiation with light, an increase in the $CO_2$ content in the atmosphere in contact with said plant and combinations thereof.

5. The method according to claim 1, wherein,
    production and excretion of said metabolites synthesized by said plants are increased by neosynthesis of said metabolites after addition of metabolite precursors, and
    said precursors are added to said plants by including said precursors in said nutritional solution added in the region of said roots or said precursors are sprayed onto said top growth in a mixture with surfactants to obtain foliar penetration.

6. The method according to claim 1, wherein, production and excretion of said metabolites are increased by forcing photosynthetic activity by exposing said plants to artificial lighting for a period longer than that to which said plants are accustomed.

7. The method according to claim 1, wherein,
    said metabolites are obtained from said top growth by showering or spraying said plants with a solution or liquid containing surfactants, surface-active agents and/or detergents, and
    charged showering or spraying solution is recovered separately or in a mixture with said nutrient solution for extraction and purification of said metabolites.

8. The method according to claim 1, wherein, said plants are higher or vascular plants adapted to synthesize metabolites.

9. A method of producing molecules from plants with top growth and root growth, comprising the steps of:
    providing a plurality of containers (2) for the soil-less culture of plants (1);
    providing a device for the storage and contribution of nutrient solution (3) for said plants (1), comprising a reservoir (13) and a distribution line (13') associated with a network of conduits (13") carrying said solution (3) in a controlled manner to the base of said plants (1);
    providing a distribution device for permeabilization solution and/or leaching liquid comprising a reservoir for mixing and storage (14) of the permeabilization solution and/or a reservoir (14') for the leaching liquid, associated with lines for distribution (14") by spraying and/or injection;

providing an assembly of means (15, 15', 15", 16) for recovery, treatment and recycling at least of spent nutrient solution (3'), said means for recovery, treatment and recycling consisting of an intermediate storage tank (15) collecting spent nutrient solution (3') discharged by drainage of said containers (2) and connected by a direct recycling line (15') and by a second recycling line (15") comprising a unit (16) for separation or extraction in a loop for reinjection into said storage reservoir (13) of nutrient solution (3), said unit (16) extracting said metabolites contained in said spent nutrient solution (3') and liberated by said roots and/or top growth of said plants (1);

cultivating said plants in soil-less and non-sterile conditions;

feeding said plants with a nutrient solution and/or spraying said plants with a leaching liquid;

recovering and treating said solution and/or said liquid to extract therefrom secondary metabolites liberated by roots and/or top growth of said plants, said metabolites being selected from the group consisting of tropane and indole type alkaloids, anti-cancer agents, taxanes or taxol derivatives, furocoumarins, terpenes, glycosides, phenyl propanoids, saponines and steroids;

recovering said extracted metabolites;

forcing permeabilization of said roots or top growth with a permeabilizing solution containing salts, surfactants, detergents, solvents, elicitors or fungal or bacterial origin, derivatives of jasmonic acid or other products which stimulate the natural defenses of plants; and repeating said steps of forcing permeablization, recovering and treating said solution and/or liquid to extract metabolites, and recovering said extracted metabolites until a desired amount of metabolites have been recovered from said plants, wherein, said forcing permeabilization step is carried out continuously by adding said permeabilizing solution to said nutrient solution supplied continuously or at regular intervals to said plants such that flows issuing from said roots and/or top growth toward and into spent nutrient solution and/or charged leaching liquid contain said metabolites and are significantly increased without loss of viability of said plants, said forcing permeabilization step does not lead, even partially, to the destruction of said plants.

10. The method according to claim 9, further comprising the step of:

supplying said reservoir (13) by an injection line (13''') for additional nutrient substances stored in suitable reservoirs (13''''), so as to compensate for quantities of such substances removed by said plants (1').

11. The method according to claim 9, further comprising the steps of:

initiating plant cultivation in soil-less conditions to allow growth and development of said plants;

recovering said metabolites liberated by said roots or top growth using a liquid which is brought into contact with said roots by percolation or immersion or with leaves of said plants by spraying;

collecting spent or charged solution in percolated form from said roots or leached form from said leaves;

isolating desired metabolites contained in said collected solution by liquid/liquid or liquid/solid extraction, recrystallization, sublimation or evaporation of water.

12. The method according to claim 9, further comprising the steps of:

rinsing of said roots and/or top growth of said plants after forcing permeabilization; and returning said rinsed plants to growth conditions for a time which is just sufficient for carrying out a further forced permeabilization treatment, followed or accompanied by a step of recovering said metabolites.

13. The method according to claim 9, further comprising the step of:

increasing the biosynthesis capacities of said plants and potential to release metabolites in the solution by a physical treatment selected from the group consisting of a rise in temperature, additional or extended irradiation with light, an increase in the $CO_2$ content in the atmosphere in contact with said plant and combinations thereof.

14. The method according to claim 9, wherein, production and excretion of said metabolites synthesized by said plants are increased by neosynthesis of said metabolites after addition of metabolite precursors, and said precursors are added to said plants by including said precursors in said nutritional solution added in the region of said roots or said precursors are sprayed onto said top growth in a mixture with surfactants to obtain foliar penetration.

15. The method according to claim 9, wherein, production and excretion of said metabolites are increased by forcing photosynthetic activity by exposing said plants to artificial lighting for a period longer than that to which said plants are accustomed.

16. The method according to claim 9, wherein, said metabolites are obtained from said top growth by showering or spraying said plants with a solution or liquid containing surfactants, surface-active agents and/or detergents, and charged showering or spraying solution is recovered separately or in a mixture with said nutrient solution for extraction and purification of said metabolites.

17. The method according to claim 9, wherein, said plants are higher or vascular plants adapted to synthesize metabolites.

* * * * *